United States Patent
Oku

(10) Patent No.: US 9,440,075 B2
(45) Date of Patent: Sep. 13, 2016

(54) SWALLOWING ASSIST DEVICE

(71) Applicant: HYOGO COLLEGE OF MEDICINE, Nishinomiya-shi (JP)

(72) Inventor: Yoshitaka Oku, Nishinomiya (JP)

(73) Assignee: HYOGO COLLEGE OF MEDICINE, Nishinomiya-Shi (JP)

( * ) Notice: Subject to any disclaimer, the term of this patent is extended or adjusted under 35 U.S.C. 154(b) by 0 days.

(21) Appl. No.: 14/629,489

(22) Filed: Feb. 24, 2015

(65) Prior Publication Data

US 2015/0165201 A1 Jun. 18, 2015

Related U.S. Application Data

(63) Continuation of application No. PCT/JP2013/072452, filed on Aug. 22, 2013.

(30) Foreign Application Priority Data

Sep. 7, 2012 (JP) .................... 2012-197483

(51) Int. Cl.
*A61N 1/36* (2006.01)
*A61B 5/08* (2006.01)
(Continued)

(52) U.S. Cl.
CPC ......... *A61N 1/36067* (2013.01); *A61B 5/0816* (2013.01); *A61N 1/0456* (2013.01);
(Continued)

(58) Field of Classification Search
CPC ........... A61N 1/3601; A61N 1/36139; A61N 1/3606; A61N 1/3611; A61N 1/36175; A61N 1/36135; A61N 1/36132; A61N 1/37; A61N 1/36128; A61N 1/3925; A61N 1/02; A61N 1/36; A61N 1/36178; A61N 1/365; A61N 1/36146; A61B 5/4836; A61B 5/0816; A61B 5/08; A61B 5/7282; A61B 5/0205; A61B 5/087; A61B 5/003; A61B 5/04; A61B 5/05; A61B 5/4205; A61B 5/4848; A61B 5/00; A61B 5/0482; A61B 5/0484; A61B 5/082

See application file for complete search history.

(56) References Cited

U.S. PATENT DOCUMENTS 5,725,564 A 3/1998 Freed et al.
7,917,206 B2 * 3/2011 Frei .................... A61B 5/04012
607/2

(Continued)

FOREIGN PATENT DOCUMENTS

JP 09-215757 A 8/1997
JP 11-500339 A 1/1999
(Continued)

OTHER PUBLICATIONS

Shaker et al., "Coordination of deglutition and phases of respiration: effect of aging, tachypnea, bolus volume, and chronic obstructive pulmonary disease", American Journal of Physiology 263, 1992, pp. G750-G755.

(Continued)

*Primary Examiner* — Deborah Malamud
(74) *Attorney, Agent, or Firm* — Mori & Ward, LLP

(57) ABSTRACT

A swallowing assist device for assisting swallowing includes a respiration detection part, an application unit, and a control part. The respiration detection part detects respiration. The application unit is attached to a target section to apply a stimulus for facilitation of swallowing. The control part controls the application unit. The control part controls the application unit to start application of the stimulus to the target section during an expiration period detected according to a detection signal from the respiration detection part, and terminate the application of the stimulus to the target section during the expiration period.

14 Claims, 11 Drawing Sheets

(51) Int. Cl.
*A61N 1/04* (2006.01)
*A61N 1/32* (2006.01)
*A61N 1/05* (2006.01)

(52) U.S. Cl.
CPC .......... *A61N1/0476* (2013.01); *A61N 1/0492* (2013.01); *A61N 1/323* (2013.01); *A61N 1/36003* (2013.01); *A61N 1/36007* (2013.01); *A61N 1/36014* (2013.01); *A61N 1/36139* (2013.01); *A61N 1/0507* (2013.01); *A61N 1/3611* (2013.01)

(56) References Cited

U.S. PATENT DOCUMENTS

| | | | |
|---|---|---|---|
| 2004/0230252 A1* | 11/2004 | Kullok | A61M 21/00 607/48 |
| 2007/0156182 A1 | 7/2007 | Castel et al. | |
| 2008/0147142 A1 | 6/2008 | Testerman et al. | |
| 2009/0187124 A1 | 7/2009 | Ludlow et al. | |

FOREIGN PATENT DOCUMENTS

| | | |
|---|---|---|
| JP | 2007-151736 A | 6/2007 |
| JP | 4526472 B2 | 6/2007 |
| JP | 2008-544832 A | 12/2008 |
| JP | 2009-522059 A | 6/2009 |
| JP | 2010-512843 A | 4/2010 |
| WO | WO 97/15349 | 5/1997 |
| WO | WO 2008/076646 | 6/2008 |

OTHER PUBLICATIONS

Paydarfar et al., "Respiratory phase resetting and airflow changes induced by swallowing in humans", The Journal of Physiology 483, Pt 1, 1995, pp. 273-288.

International Search Report for corresponding International Application No. PCT/JP2013/072452, Oct. 15, 2013.

Written Opinion for corresponding International Application No. PCT/JP2013/072452, Oct. 15, 2013.

* cited by examiner

SWALLOWING ASSIST DEVICE

CROSS-REFERENCE TO RELATED APPLICATIONS

The present application is a continuation application of International Application No. PCT/JP2013/072452, filed Aug. 22, 2013, which claims priority to Japanese Patent Application No. 2012-197483, filed Sep. 7, 2012. The contents of these applications are incorporated herein by reference in their entirety.

BACKGROUND OF THE INVENTION

1. Field of the Invention

The present invention relates to a swallowing assist device.

2. Disclosure of Related Art

In recent years, pneumonia has been exponentially increasing as a cause of death from disease. Most of pneumonic diseases resulting in death are aspiration pneumonia caused by so-called "aspiration." In particular, aspiration pneumonia in elderly people has been a severe problem. The "aspiration" refers to a disease state in which swallowing cannot be done appropriately and the swallowed thing enters the trachea, not the esophagus. It is an important issue to prevent aspiration of especially elderly people to avoid aspiration pneumonia.

In general, aspiration is caused more frequently by aspirating saliva while asleep rather than at mealtimes. During the act of swallowing, pathogenic bacteria adhered to the saliva may enter the trachea to cause aspiration pneumonia. It is known that the patients of aspiration pneumonia show high thresholds at which to induce swallowing, that is, they hardly cause a swallowing reflex. Therefore, aspiration pneumonia can be effectively prevented by inducing a swallowing reflex to encourage proper swallowing.

As one of devices for inducing a swallowing reflex, there is known a device for facilitating swallowing by applying an electric stimulus to the patient's larynx, for example.

To suppress aspiration pneumonia, it is necessary to continuously apply an electric stimulus to the patient for a relatively long time such as during sleep hours, for example. However, if an electric stimulus is continuously and monotonically applied to the patient during that time, the application of an electric stimulus may induce swallowing in an inspiratory phase during which the patient breathes in, for example. However, when swallowing occurs in the inspiratory phase, the swallowed thing with the inspired air may enter the trachea at a higher risk, and thus aspiration may be more likely to occur.

SUMMARY OF THE INVENTION

According to one aspect of the present invention, a swallowing assist device for assisting swallowing includes a respiration detection part, an application unit, and a control part. The respiration detection part detects respiration. The application unit is attached to a target section to apply a stimulus for facilitation of swallowing. The control part controls the application unit. The control part controls the application unit to start application of the stimulus to the target section during an expiration period detected according to a detection signal from the respiration detection part, and terminate the application of the stimulus to the target section during the expiration period.

BRIEF DESCRIPTION OF THE DRAWINGS

Advantages and significance of the present invention will be more clarified by the following descriptions of embodiments. However, the embodiments described below are merely examples of carrying out the present invention, and the present invention is not limited by the following embodiments.

A more complete appreciation of the invention and many of the attendant advantages thereof will be readily obtained as the same becomes better understood by reference to the following detailed description when considered in connection with the accompanying drawings, wherein.

Figure 1:
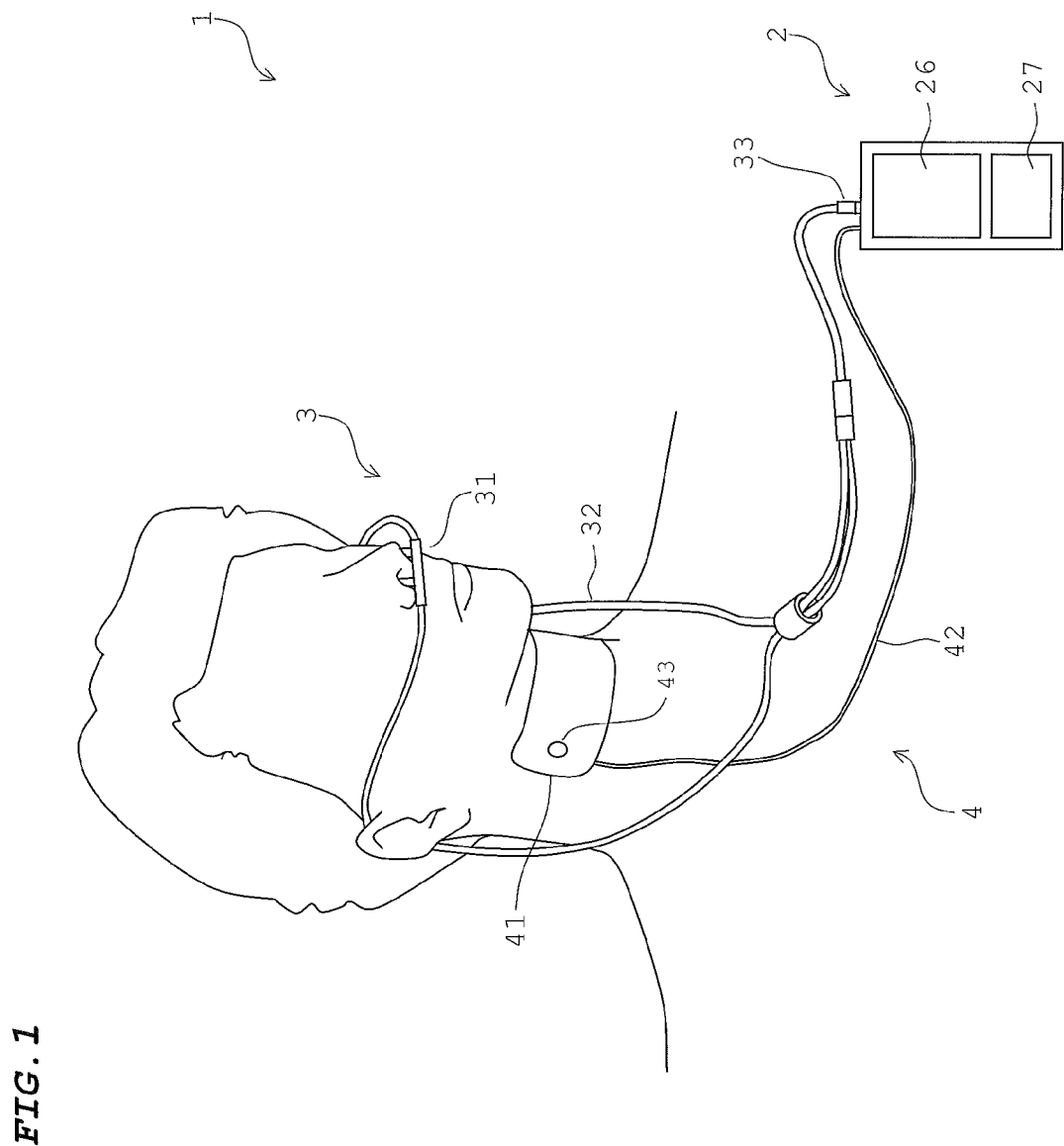
FIG. 1 is a diagram illustrating an outer appearance of a swallowing assist device according to an embodiment.

However, the drawings are merely intended for description and are not intended to limit the scope of the invention.

DESCRIPTION OF THE EMBODIMENTS

The embodiments will now be described with reference to the accompanying drawings, wherein like reference numerals designate corresponding or identical elements throughout the various drawings.

An embodiment of the present invention is applied to a swallowing assist device for causing proper swallowing. Hereinafter, a swallowing assist device 1 according to the embodiment will be described with reference to the accompanying drawings.

In the embodiment described below, a pressure sensor 24 corresponds to a "respiration detection part" described in the claims; a display part 26 and an input part 27 correspond to an "acceptance part" described in the claims; and an electrode unit 4 corresponds to an "application unit" described in the claims. However, the correspondences between the claims and the descriptions of the embodiment are merely examples and are not intended to limit the inventions described in the claims.

FIG. 1 is a diagram illustrating an outer appearance of the swallowing assist device 1 according to the embodiment. The swallowing assist device 1 is provided with a control unit 2, a nasal cannula 3, and an electrode unit 4.

The control unit 2 includes a display part 26 and an input part 27, and is configured to be small in size and weight so that the patient can constantly wear the swallowing assist device 1. The user inputs an instruction to the control unit 2 from the input part 27 while viewing display on the display part 26. The input part 27 is composed of buttons and adjustment knobs.

The nasal cannula 3 includes an attachment part 31 with a pair of cylindrical members, a tube 32 coupled to both ends of the attachment part 31, and a connection part 33 provided at a tip of the tube 32. The pair of cylindrical members in the attachment part 31 is inserted into the patient's nasal cavity, and the connection part 33 is connected to the control unit 2. Accordingly, when the patient breathes and the air flows in the tube 32, the airflow in the tube 32 is detected as a pressure by the pressure sensor 24 of the control unit 2 (refer to FIG. 2). Even when the patient takes breathes through the mouth, since the nasal cavity and the mouth cavity are connected to each other, the air flows in the tube 32 and causes a pressure change.

The electrode unit 4 includes a thin and flexible pad 41, a cable 42, and electrodes 43 provided on the pad 41. Each of the electrodes 43 is thin and flexible, and one of the electrodes 43 is positive pole and the other is negative pole (refer to FIG. 2). The electrodes 43 are connected to the control unit 2 via the cable 42. When the electrodes 43 are driven by the control unit 2, electric current flows between the positive and negative poles of the electrodes 43 to facilitate a swallowing reflex.

Figure 2:
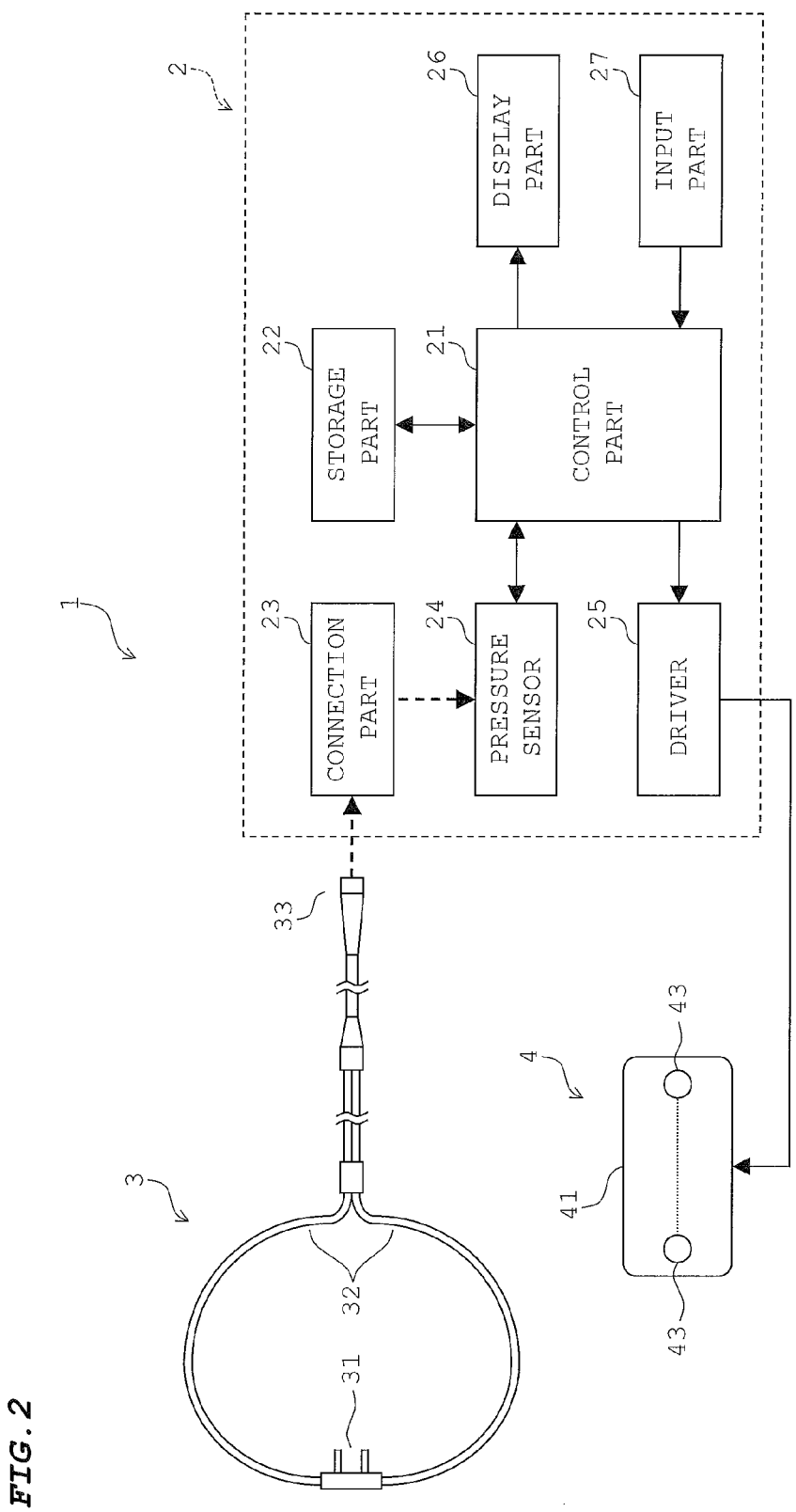
FIG. 2 is a diagram illustrating a configuration of a control unit according to the embodiment.

FIG. 2 is a diagram illustrating a configuration of the control unit 2.

The control unit 2 includes a control part 21, a storage part 22, a connection part 23, the pressure sensor 24, and a driver 25 as well as the display part 26 and the input part 27 illustrated in FIG. 1.

The control part 21 executes computer programs stored in the storage part 22 to control the components of the control unit 2. The storage part 22 stores the computer programs to be executed by the control part 21 and is also used as a working area for the control part 21 to perform processes.

The connection part 23 is connected to the connection part 33 of the nasal cannula 3. The connection part 23 guides the air from the tube 32 of the nasal cannula 3 to the pressure sensor 24. The pressure sensor 24 detects the flow of the air guided by the connection part 23 as a pressure. The detection signal from the pressure sensor 24 is transmitted to the control part 21. The driver 25 drives the electrodes 43 of the electrode unit 4 under the control of the control part 21.

To facilitate a swallowing reflex by an electric stimulus using the electrode unit 4 illustrated in FIG. 2, there are various conventionally known methods by which electric stimulus is applied to the nerves of the upper pharynx or is applied to the swallowing muscles, or the like. In addition, referring to FIG. 2, the pair of electrodes 43 is arranged on the pad 41. However, the number of the electrodes 43 on the pad 41 is not limited to the foregoing one. For example, two pairs of positive and negative electrodes may be arranged on the pad 41 as illustrated in FIG. 3A.

Hereinafter, a method for facilitating swallowing with the use of the pad 41 illustrated in FIG. 3A will be described.

Figure 3A:
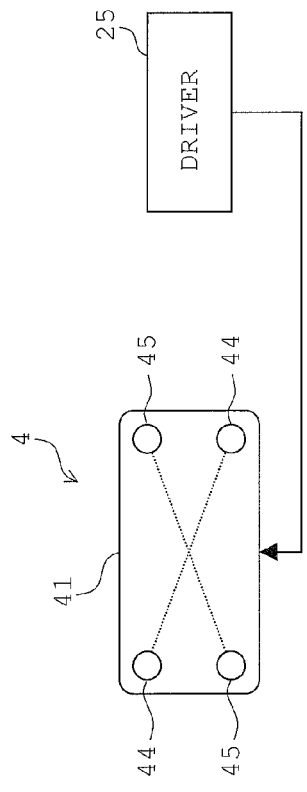
FIGS. 3A to 3D are diagrams illustrating modification examples of an electrode unit according to the embodiment.

Referring to FIG. 3A, the pad 41 of the electrode unit 4 is thin and flexible and is provided with electrodes 44 composed of positive and negative poles (one pair of poles) and electrodes 45 composed of positive and negative poles (one pair of poles). The pad 41 is attached to the patient's skin in such a manner that the positive and negative poles of the electrodes 44 and 45 are arranged in an X-formation around the thyroid cartilage. The electrodes 44 and 45 are each driven at medium frequencies such that the difference between the frequencies of the electrodes 44 and 45 is a low frequency. Accordingly, a low-frequency interference wave occurs at the deep portion according to the difference between the frequencies, and the superior laryngeal nerve is stimulated by the interferential current.

Figure 3B:
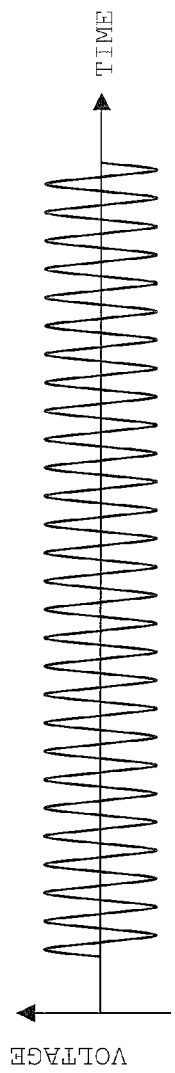
Figure 3C:
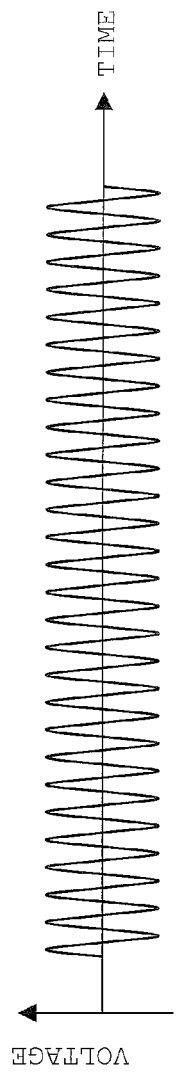
Figure 3D:
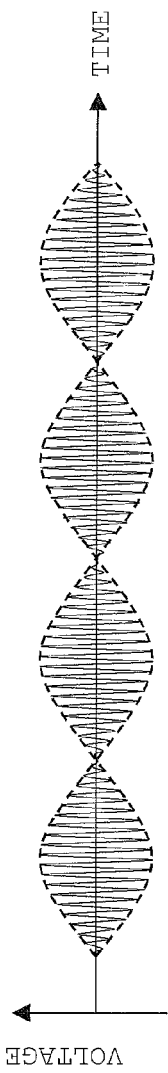

FIGS. 3B and 3C are diagrams schematically illustrating sinusoidal signals of voltages applied to the electrodes 44 and 45 with the frequencies of the electrodes 44 and 45 respectively set to 2000 Hz and 2050 Hz. As illustrated by dashed lines in FIG. 3D, an interference wave of 50 Hz occurs according to the difference between the frequencies of the electrodes 44 and 45. Accordingly, an afferent signal transferred from the pharynx and larynx to the brain stem through the superior laryngeal nerve is enhanced, thus a swallowing reflex is facilitated. By using the interference wave resulting from the two pairs of electrodes as described above, it is possible to effectively facilitate swallowing while suppressing pain and discomfort in the skin.

Even when the one pair of electrodes 43 is used as illustrated in FIG. 2, the same interference wave as that in the case of using the pad 41 illustrated in FIG. 3A can be applied to the superior laryngeal nerve by adjusting the waveform of a drive signal to be applied to the electrodes 43 so as to become a burst-modulated alternating waveform.

In the configuration illustrated in FIG. 3A, the frequencies of the electrodes 44 and 45 are set between 2000 Hz and 2050 Hz. If the frequencies are set to be lower than 500 Hz, the subcutaneous nociceptors react strongly to that to make pain likely to be delivered to the central nervous system. On the other hand, if the frequencies are set to be higher than 8000 Hz, muscle contraction continues to occur because it cannot follow each of stimulating pulses. Accordingly, the frequencies of the electrodes 44 and 45 are set within the range described above.

In the configuration illustrated in FIG. 3A, the difference between the frequencies of the electrodes 44 and 45 is set between 10 Hz and 50 Hz. When the difference between the frequencies of the electrodes 44 and 45 is set as described above, the swallowing-related receptors, mainly Aδ fibers, react strongly and thus the stimulation from the electrodes 44 and 45 becomes effective afferent nerve impulses (from the pharynx and larynx to the brain).

In addition, in the configuration illustrated in FIG. 3A, output current to the electrodes 44 and 45 is set between 1 mA and 3 mA. When the output current to the electrodes 44 and 45 is set as described above, the current is more likely to reach the superior laryngeal nerve as compared to the case where the output current is set to be lower than 1 mA. In addition, it is possible to prevent application of an excessive stimulus to the superior laryngeal nerve as compared to the case where the output current is set to be higher than 3 mA.

The period of time during which the electrode signals illustrated in FIGS. 3B and 3C are applied to the electrodes 44 and 45 for facilitation of swallowing is desirably set between 100 ms and 1000 ms. By setting the time for applying the electrode signals to be equal to or higher than 100 ms, the superior laryngeal nerve can be sufficiently stimulated. In addition, by setting the time for applying the electrode signals to be equal to or lower than 1000 ms, it is possible to keep the time for applying the electrode signals to be equal to or less than half the period of the expiratory phase. Specifically, in general, a human's breathing cycle is three seconds, of which the two seconds is in the expiratory phase and the one second is in the inspiratory phase. Therefore, when the period of the time for applying the electric signals is 1000 ms (one second), the superior laryngeal nerve is stimulated during almost half the period of the expiratory phase. Accordingly, when the upper limit for the period of application of the electric signals is set as 1000 ms, the period during which the superior laryngeal nerve is stimulated can be easily kept within the first half of the expiratory phase in the case where the application of the electric signals is started immediately after the start of the expiratory phase or within a short time after the start of the expiratory phase. This makes it possible to effectively suppress induction of aspiration by providing sufficient pause before the next inspiration. Control of driving of the electrode unit 4 (electrodes 44 and 45) will be described later with reference to FIG. 5B.

Next, it will be discussed below on the desired timing at which to induce swallowing in the case of facilitating for inducing by the electrode unit 4.

Figure 4B:
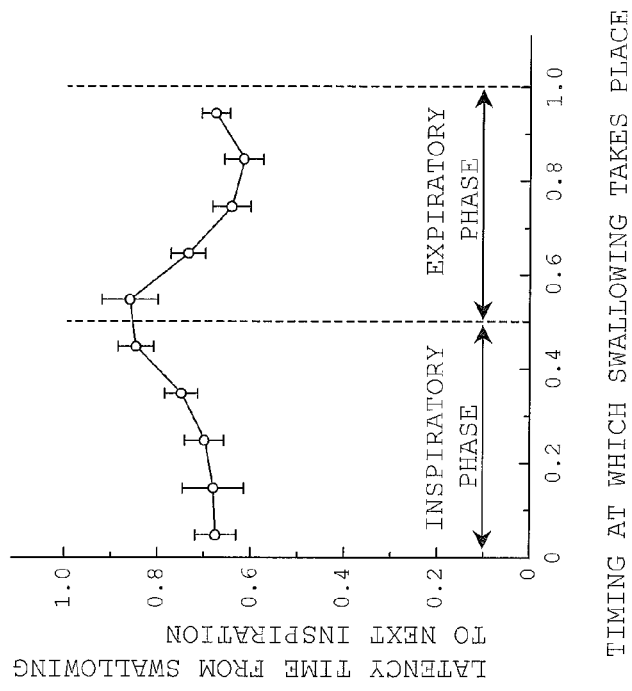
FIGS. 4A and 4B are respectively a diagram illustrating the frequencies of swallowing of young people and elderly peoples in expiratory and inspiratory phases and a diagram illustrating the relationship between the timing at which swallowing has occurred and the latency time from swallowing to next inspiration according to the embodiment.
Figure 4A:
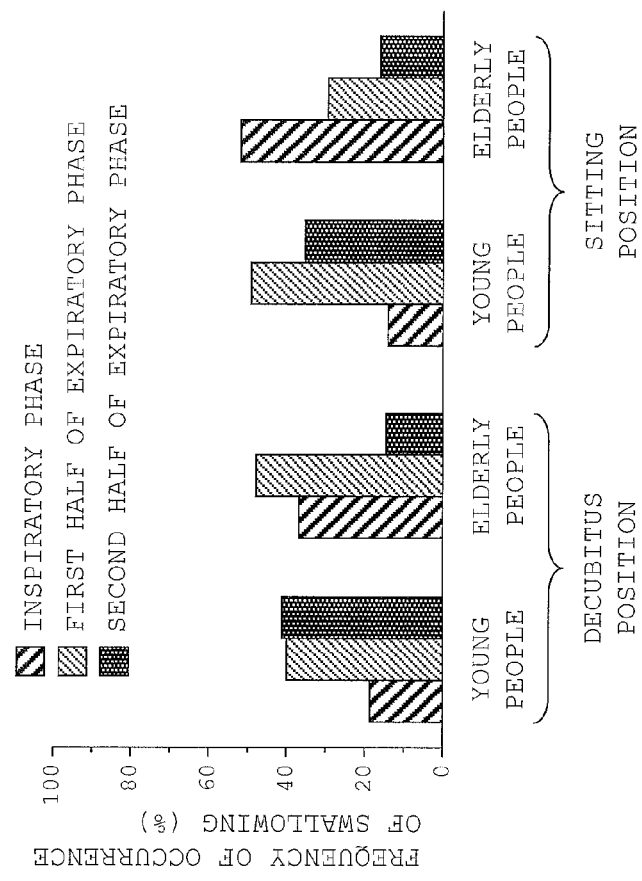

FIG. 4A is a diagram illustrating the frequencies (%) of swallowing of young people and elderly people in the expiratory and inspiratory phases. FIG. 4A shows the tendencies of occurrence of swallowing in the young people and the elderly people both in the decubitus position and in the sitting position. FIG. 4A is derived from FIG. 5 of *Coordination of deglutition and phases of respiration: effect of aging, tachypnea, bolus volume, and chronic obstructive pulmonary disease* by R. Shaker, Q. Li, J. Ren, W. F. Townsend, W. J. Dodds, B. J. Martin, M. K. Kern, A. Rynders, Am J Physiol 263:G750-5 (1992).

Referring to FIG. 4A, it can be seen that the young people performed most of swallowing acts in the expiratory phase in which they breathed out. In contrast, it can be seen that the elderly people performed swallowing acts at significantly higher frequencies in the inspiratory phase in which they breathed in, as compared to the young people. Since the elderly people perform swallowing acts in the inspiratory phase at higher frequencies as described above, they are more likely to cause aspiration as compared to the young people. Accordingly, there is a higher risk that the elderly people suffer from pneumonia caused by aspiration, that is, aspiration pneumonia.

In general, it is known that the patients of aspiration pneumonia show high thresholds at which to induce swallowing, that is, they hardly cause a swallowing reflex during nighttime. Therefore, aspiration pneumonia can be effectively suppressed by facilitating a swallowing reflex.

However, if swallowing is continuously and monotonically induced in the patient during sleep hours or the like, swallowing may be induced in an inspiratory phase during which the patient breathes in, for example. When swallowing occurs in the inspiratory phase, the swallowed thing with the inspired air may enter the trachea at a higher risk, and thus aspiration may be more likely to occur. Therefore, it is necessary to induce swallowing in the patient in the expiratory phase in which he/she breathes out.

In addition, to decide the timing for inducing swallowing, the time between the start of swallowing and the start of inspiration needs to be considered. Specifically, even when swallowing is induced in the expiratory phase in which the patient breathes out, if the time between the start of swallowing and the start of inspiration is short, the swallowing and the inspiration are likely to occur in a consecutive manner, thereby bringing about a higher possibility of aspiration. Therefore, it is necessary to set the timing for inducing swallowing of the patient according to the time between the start of swallowing and the start of inspiration.

FIG. 4B is a diagram illustrating the relationship between the timing at which swallowing has occurred and the latency time from swallowing to next inspiration. FIG. 4B is derived from FIG. 2C of *Respiratory phase resetting and airflow changes induced by swallowing in humans* by D. Paydarfar, R. J. Gilbert, C. S. Poppel, P. F. Nassab, The Journal of Physiology 483 (Pt 1):273-88 (1995).

Referring to FIG. 4B, it can be seen that the time between the occurrence of swallowing and the start of next expiration varies depending on the timing at which swallowing has occurred in the inspiratory and expiratory phases. In the expiratory phase, when swallowing occurs at the timing at which switching takes place from the inspiratory phase to the expiratory phase, the latency time until the next inspiration becomes longest, and when swallowing occurs at the timing at about ⅔ of the expiratory phase, the latency time until the next inspiration becomes shortest. Therefore, it is desired to induce swallowing at the timing except for that at about ⅔ of the expiratory phase.

From the foregoing discussion, it is considered that aspiration can be made less prone to occur by setting the timing for inducing swallowing in the first half of the expiratory phase. Based on the result of the discussion, in the embodiment, the electrode unit 4 is controlled in such a manner that an electric stimulus from the electrode unit 4 is applied to the patient at a predetermined timing in the first half of the expiratory phase. Specifically, the electrode unit 4 is controlled in such a manner that an electric stimulus is applied to the patient at the timing at which expiration reaches the peak in the first half of the expiratory phase.

Processes for controlling the electrode unit 4 will be described below with reference to FIGS. 5A, 5B, and 6. In the controlling processes of FIGS. 5A and 5B, an electric stimulus from the electrode unit 4 is applied to the patient at the timing at which expiration reaches the peak in the first half of the expiratory phase, thereby inducing swallowing.

Figure 5B:
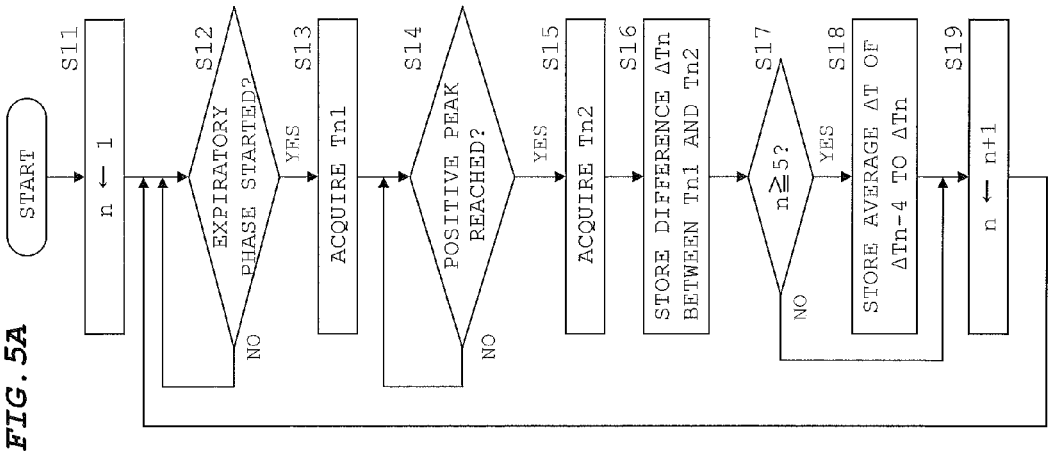
FIGS. 5A and 5B are respectively a flowchart of a process for acquiring ΔT and a flowchart of a process for controlling the electrode unit according to the embodiment.
Figure 5A:
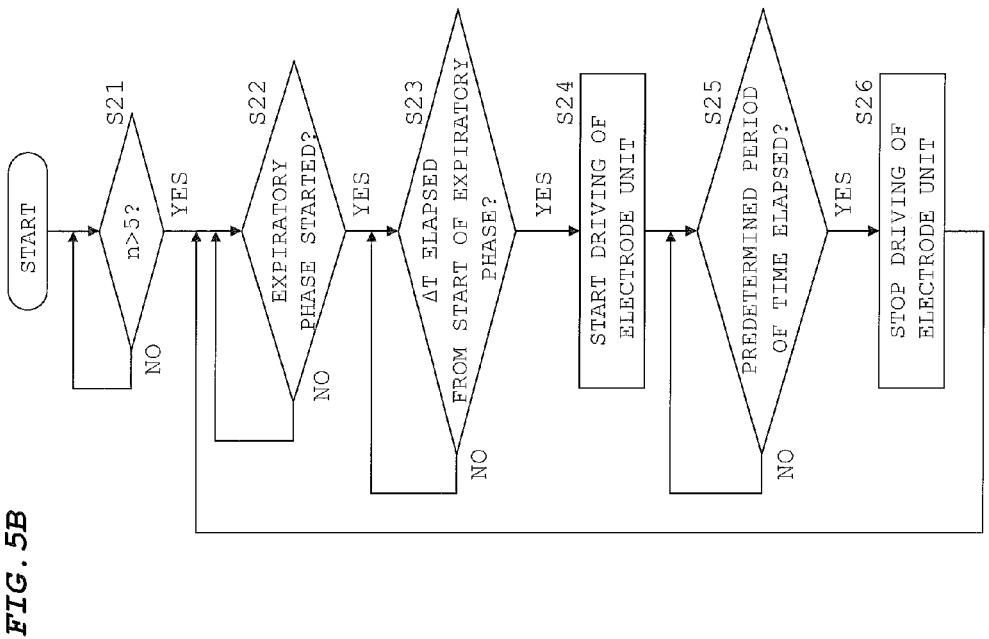
Figure 6:
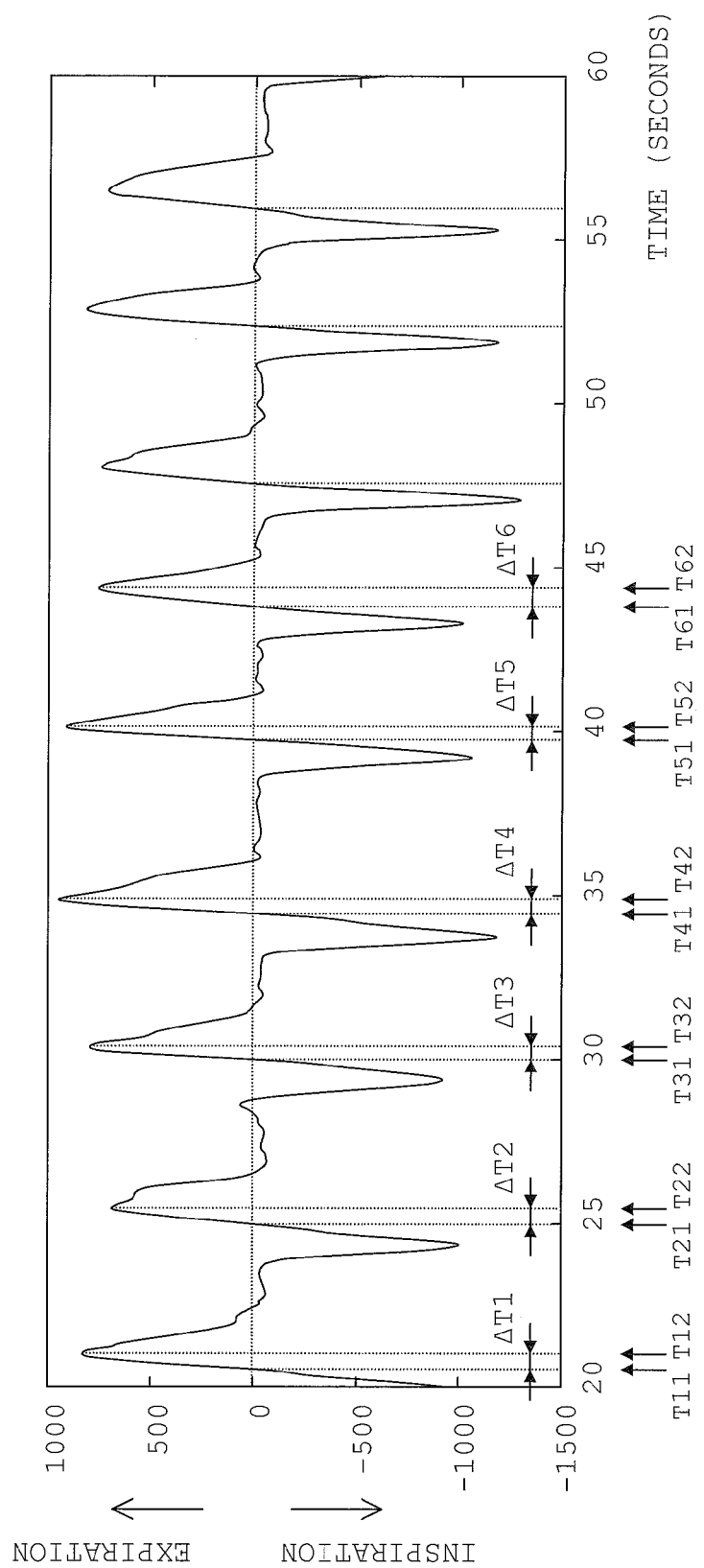
FIG. 6 is a diagram illustrating changes in respiratory volume according to the embodiment.

FIG. 5A is a flowchart of a process for acquiring a value ΔT for deciding the timing for driving the electrode unit 4, and FIG. 5B is a flowchart of a process for controlling the electrode unit 4 using the value ΔT. The controlling processes illustrated in FIGS. 5A and 5B are carried out in parallel. FIG. 6 shows changes in respiratory volume. The vertical axis shows the detection signal from the pressure sensor 24 in which the positive and negative values indicate expiration and inspiration, respectively. The horizontal axis shows the lapse of time (seconds).

Referring to FIG. 5A, when a swallowing assist act is started by the control unit 2, the control part 21 of the control unit 2 sets the value of a variable n stored in the storage part 22 to 1 (S11). Subsequently, the control part 21 determines whether the expiratory phase has started (S13). In this case, the control part 21 determines that the expiratory phase has started when the detection signal has gradually increased from the negative peak and become zero as illustrated in FIG. 6, for example.

When the expiratory phase has started (S12: YES), the control part 21 acquires an expiratory phase start time Tn1 (S13). Accordingly, an expiratory phase start time T11 with the variable n of 1 is acquired, for example (refer to FIG. 6).

Next, the control part 21 determines whether the detection signal has reached its positive peak (S14). When the detection signal has reached the positive peak (S14: YES), the control part 21 acquires a time Tn2 at which the detection signal has reached the positive peak (S15). Accordingly, a time T12 with the variable n of 1 is acquired, for example (refer to FIG. 6).

When the times Tn1 and Tn2 have been acquired as described above, the control part 21 stores a difference ΔTn between the times Tn1 and Tn2 (S16). Accordingly, a difference ΔT1 with the variable n of 1 is stored, for example (refer to FIG. 6).

Next, the control part 21 determines whether the value of the variable n is 5 or larger (S17). When the value of the variable n is smaller than 5 (S17: NO), the control part 21 skips step S18 and adds 1 to the value of the variable n (S19). Thus, the control part 21 returns the process to step S12 to repeatedly perform steps S12 to S19.

Accordingly, each time the value of variable n is increased by 1, the difference ΔTn according to the value of the variable n is stored. As illustrated in FIG. 6, for example, a difference ΔT2 between times T21 and T22, a difference ΔT3 between times T31 and T32, a difference ΔT4 between times T41 and T42, and a difference ΔT5 between times T51 and T52 are stored in sequence in the storage part 22.

When the value of the variable n has reached 5 (S17: YES), the control part 21 calculates an average value ΔT of differences ΔTn−4 to ΔTn, and stores the calculated average value ΔT in the storage part 22 (S18). Then, the control part 21 adds 1 to the value of the variable n (S19) and returns the process to step S12 to repeatedly perform steps S12 to S19. That is, when the variable n is 5, the average value ΔT of the differences ΔT1 to ΔT5 is acquired.

The thus acquired average value ΔT is the average of the times between the instant when the expiration has been started and the instant when the expiration has reached the peak with respect to the current expiratory phase and four preceding expiratory phases.

Subsequently, when the value of the variable n becomes larger than 5, each time the value of the variable n is increased by 1, the average value ΔT is re-calculated at the steps S12 to S18. The re-calculated average value ΔT is an average of the times between the instant when the expiration has started and the instant when the expiration has reached the peak with respect to the current expiratory phase and the four preceding expiratory phases. Accordingly, the average value ΔT is acquired repeatedly in each of the expiratory phases.

Referring to FIG. 5B, the control part 21 of the control unit 2 determines whether the value of the variable n stored in the storage part 22 is larger than 5 (S21). When the value of the variable n is larger than 5 (S21: YES), the control part 21 starts the steps S22 to S26.

When the value of the variable n exceeds 5 (S21: YES), the control part 21 determines whether the expiratory phase has started in the same manner as at S12 (S22). When the expiratory phase has been started (S22: YES), the control part 21 uses the latest average value ΔT stored at the step S18 of FIG. 5A at this time to determine whether the time of the average value ΔT has elapsed from the start of the expiratory phase (S23). The average value ΔT is the average value of the differences ΔTn (the time from the start of the expiratory phase to the peak of the expiration) with respect to the five expiratory phases preceding the current expiratory phase.

When the time of the average value ΔT has elapsed from the start of the expiratory phase (S23: YES), the control part 21 starts to drive the electrode unit 4 at that timing (S24). Then, the control part 21 continues to apply drive voltages illustrated in FIGS. 3B and 3C, for example, to the electrodes 44 and 45 of the electrode unit 4 until a predetermined period of time set in advance as time for facilitating swallowing has elapsed.

The predetermined period of time is set at least such that the application of an electric stimulus is stopped prior to the end of the expiratory phase, more desirably such that the application of an electric stimulus is stopped prior to about ⅔ of the expiratory phase. In the embodiment, the predetermined period of time is set such that the application of an electric stimulus is stopped prior to about ⅔ of the expiratory phase.

When the predetermined period of time has elapsed (S25: YES), the control part 21 stops driving of the electrode unit 4 (S26). Accordingly, the control part 21 returns the process to S22 to repeatedly perform the steps S22 to S26 in the next expiratory phase. After that, the control part 21 repeatedly performs the steps S22 to S26 in the same manner in each of the subsequent expiratory phases.

In the flowcharts of FIGS. 5A and 5B, the control part 21 predicts the timing at which the expiration reaches the peak (average value ΔT) from the start of the expiratory phase, based on the five differences ΔTn preceding the current timing. For example, as illustrated in FIG. 6, in the case where the variable n is 6, when the control part 21 acquires an expiratory phase start time T61, the control part 21 predicts the timing at which the expiration reaches the peak, as the timing at which the time of the average value ΔT (average value of the differences ΔT1 to ΔT5) has elapsed from the expiratory phase start time T61, and then the control part 21 starts to drive the electrode unit 4 at that timing.

As described above, according to the embodiment, the electrode unit 4 is driven to facilitate swallowing in the first half of the expiratory phase, that is, in the period of time during which aspiration is considered to be further less prone to occur in the expiratory phase. Since the electrode unit 4 is driven only in the period of time during which aspiration is considered to be unlikely to occur, it is possible to prevent aspiration more effectively as compared to the case where the electrode unit 4 is continuously driven throughout the inspiratory and expiratory phases. In addition, since the electrode unit 4 is driven only in that period of time, it is possible to prevent effectively aspiration of elderly people with higher tendencies to perform swallowing in the inspiratory phase. Therefore, according to the embodiment, it is possible to assist the patients in swallowing while preventing aspiration.

Specifically, the embodiment provides advantages described below.

During the period of expiration, application of an electric stimulus is started and terminated. Accordingly, swallowing is facilitated in the period of expiration during which the patient breathes out, which reduces the possibility of aspiration by the facilitated swallowing. This makes it possible to suppress aspiration in an effective manner.

In addition, the timing for starting application of an electric stimulus falls within the first half of the expiratory phase. Accordingly, it is possible to suppress effectively the possibility of aspiration as described above with reference to FIG. 4B. Further, the application of an electric stimulus is started at the timing at which the expiration has reached the peak. When swallowing takes place around at the timing at which the expiration has reached the peak, the period of time until the inspiration occurs after the swallowing becomes longer in particular. Accordingly, by facilitating swallowing at the timing at which the expiration has reached the peak as described above, it is possible to suppress the possibility of aspiration by the facilitated swallowing in a further effective manner.

In addition, the timing for terminating the application of an electric stimulus is set to be earlier than the timing at 2/3 of the first half of the expiratory phase. Accordingly, the period of application of an electric stimulus does not overlap the time at which the latency time after the start of swallowing until the next expiration becomes shortest, thereby suppressing further effectively the possibility of aspiration by the facilitated swallowing.

As described above, the period of time (predetermined period of time) from the start to the end of application of an electric stimulus is desirably set between 100 ms and 1000 ms. Accordingly, the superior laryngeal nerve can be sufficiently stimulated. In addition, when application of an electric signal is to be started immediately after the start of the expiratory phase or within a short time after the start of the expiratory phase, the period of time during which the superior laryngeal nerve is stimulated can easily fall within the first half of the expiratory phase. This makes it possible to suppress effectively induction of aspiration by the electric stimulus.

In addition, according to the embodiment, the electrode unit 4 illustrated in FIG. 2 or 3A includes electrodes with a pair of positive and negative poles that are attached to the patient's skin for application of an electric stimulus to the superior laryngeal nerve. Accordingly, the electrode unit 4 can be attached to the target section in a simple and easy manner.

In addition, according to the embodiment, the pad 41 of the electrode unit 4 illustrated in FIG. 3A has the electrodes 44 and 45 to which electric signals at different frequencies are applied. Thus, a low-frequency interference wave occurs at the deep portion according to the difference between these frequencies, which stimulates the superior laryngeal nerve. Then, an afferent signal transferred from the pharynx and larynx to the brain stem through the superior laryngeal nerve is enhanced, thus a swallowing reflex is facilitated. Accordingly, by using an interference wave resulting from the two pairs of electrodes, it is possible to facilitate swallowing in an effective manner while suppressing pain and discomfort in the patient's skin.

In addition, according to the embodiment, the driving of the electrode unit 4 is stopped after the predetermined period of time has elapsed from the start of the driving, and then the electrode unit 4 remains stopped until the timing at which the time of $\Delta T$ has elapsed from the start of the expiratory phase. Accordingly, it is possible to suppress the patient's discomfort and pain due to the electric stimulus and alleviate the patient's burden as compared to the case where the electrode unit 4 is continuously driven throughout the inspiratory and expiratory phases.

When the electrode unit 4 includes two pairs of electrodes, the electrode unit 4 is desirably configured to be attached to the patient's skin such that the electrodes 44 and 45 are positioned in the X formation around the thyroid cartilage, as described above with reference to FIG. 3A. Accordingly, it is possible to effectively apply an electric stimulus to the superior laryngeal nerve without pain by adjusting the voltages to be applied to the two pairs of electrodes.

As in the foregoing, the embodiment of the present invention is described. However, the present invention is not limited to the foregoing embodiment. In addition, the embodiment of the present invention can be modified in various manners other than the foregoing ones.

Figure 7A:
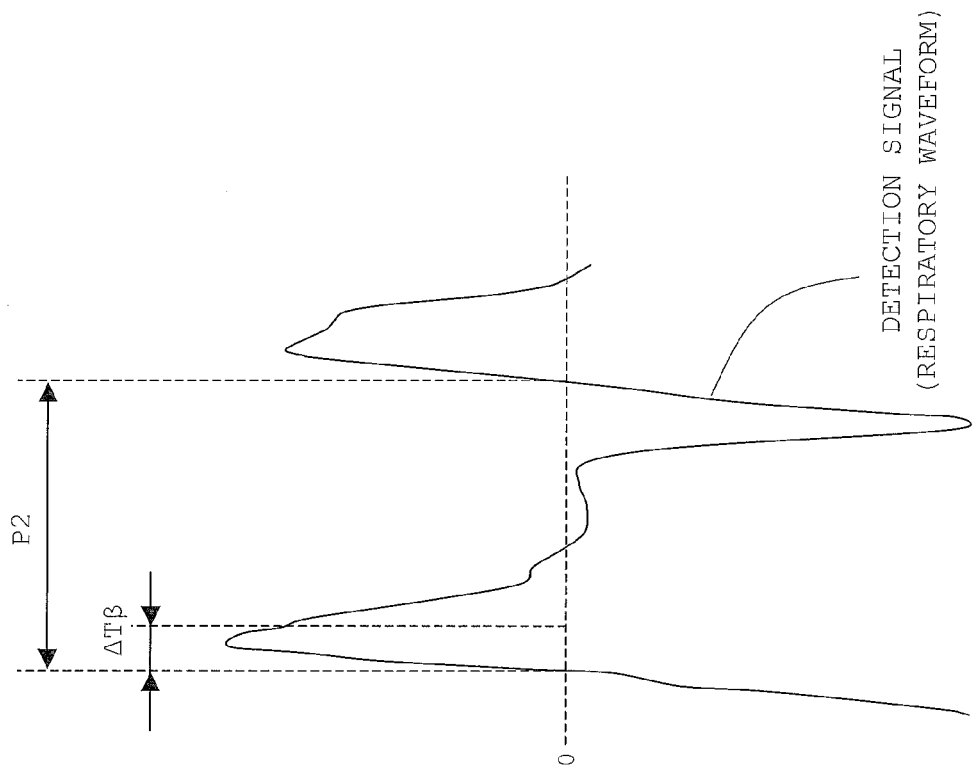
FIGS. 7A and 7B are diagrams describing methods for setting the timing for application of an electric stimulus according to a modification example.

For example, in the foregoing embodiment, the application of an electric stimulus is started to induce the patient's swallowing at the timing at which the expiration has reached the peak during the period of time of the expiratory phase. However, the timing for applying an electric stimulus is not limited to this. For example, as illustrated in FIG. 7A, the application of an electric stimulus may be started at the timing at which a time $\Delta T\alpha$ corresponding to a predetermined proportion $\alpha$ (for example, 1/3) of a period P1 of the expiratory phase has elapsed from the start of the expiratory phase. In this case, as in the foregoing embodiment, the average value of the determined times $\Delta T\alpha$ of five expiratory phases preceding the current expiratory phase can be used as time $\Delta T\alpha$ of the current expiratory phase.

Figure 7B:
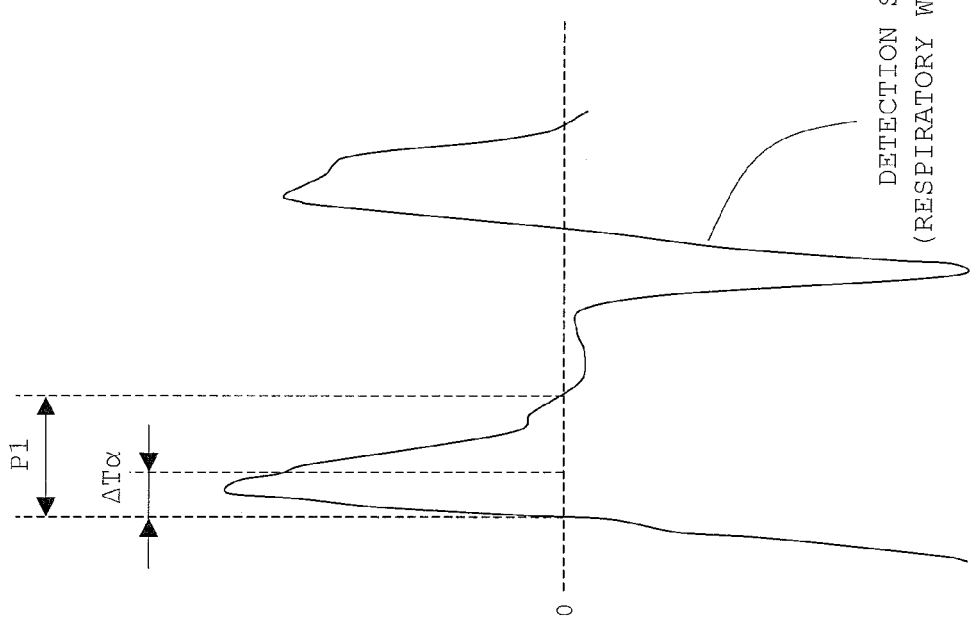

Alternatively, as illustrated in FIG. 7B, the application of an electric stimulus may be started at the timing at which a time $\Delta T\beta$ corresponding to a predetermined proportion $\beta$ (for example, 1/8) of a period P2 of the expiratory phase has elapsed from the start of the expiratory phase. In this case, as in the foregoing embodiment, the average value of the determined times $\Delta T\beta$ of five expiratory phases preceding the current expiratory phase can be used as time $\Delta T\beta$ of the current expiratory phase.

When the time $\Delta T\beta$ is decided as illustrated in FIG. 7B, the proportion $\beta$ is set in such a manner that the timing at which the time $\Delta T\beta$ has elapsed from the start of the expiratory phase falls within at least the period of the expiratory phase. In addition, when the time $\Delta T\alpha$ and the time $\Delta T\beta$ are decided as illustrated in FIGS. 7A and 7B, the proportions $\alpha$ and $\beta$ are desirably set in such a manner that the timing at which the time $\Delta T\alpha$ or the time $\Delta T\beta$ has elapsed from the start of the expiratory phase falls within the first half of the expiratory phase.

In the embodiment, the period of time during which an electric stimulus is applied is the predetermined period of time set in advance (refer to S25 of FIG. 5B). However, the period of time during which an electric stimulus is applied may be decided according to the timing at which the inspiratory phase has been started.

Figure 8B:
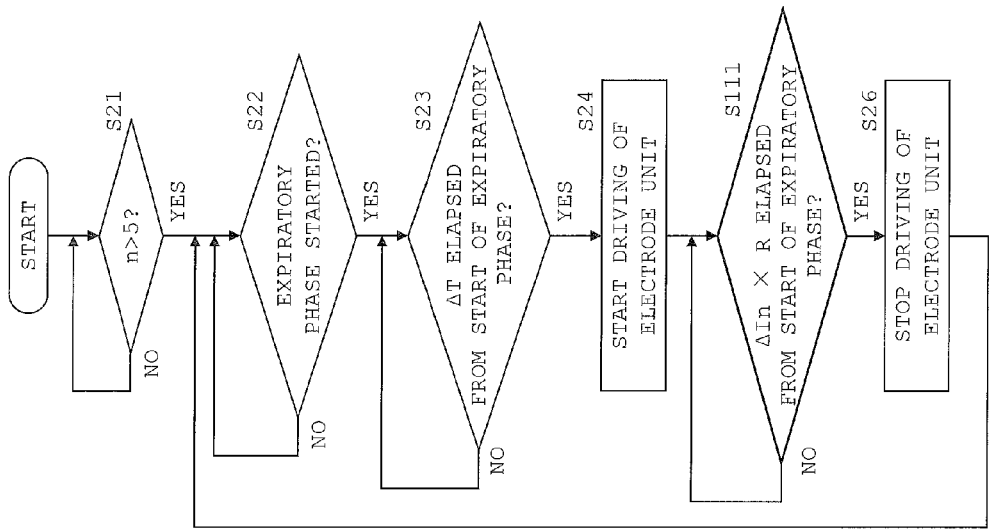
FIGS. 8A and 8B are respectively a flowchart of a process for acquiring ΔT and ΔI, and a flowchart of a process for controlling an electrode unit according to the modification example.
Figure 8A:
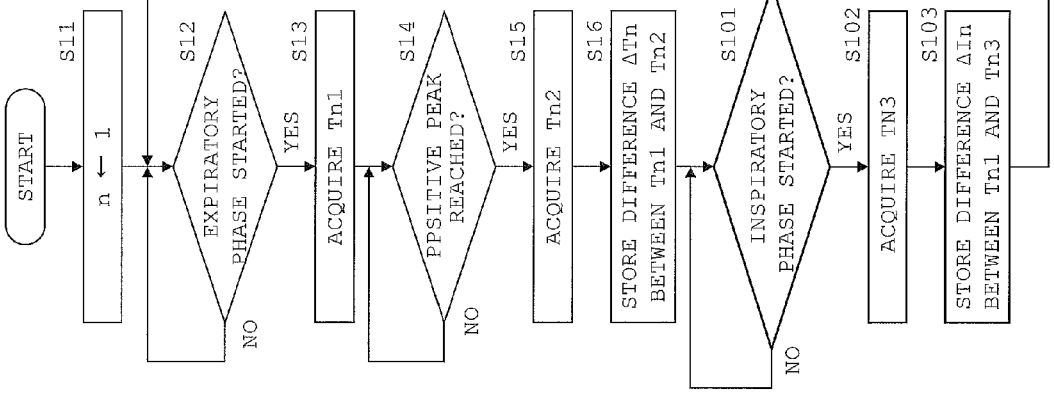

FIGS. 8A and 8B are flowcharts of processes for controlling the electrode unit 4 in this case. In this case, the processes shown in FIGS. 8A and 8B are performed instead of the processes shown in FIGS. 5A and 5B, respectively. The process in FIG. 8A includes additional steps S101 to S104 as compared to the process in FIG. 5A, and the process in FIG. 8B includes an additional step S111 as compared to the process in FIG. 5B.

Referring to FIG. 8A, after the control part 21 stores the difference $\Delta Tn$, the control part 21 determines whether the inspiratory phase has been started (S101). In this case, the control part 21 determines that the inspiratory phase has been started when the detection signal has been gradually decreased and become zero, as illustrated in FIG. 6, for example. When the inspiratory phase has been started (S101: YES), the control part 21 acquire the start time Tn3 of the inspiratory phase (S102), and stores a difference $\Delta In$ between the times Tn1 and Tn3 in the storage part 22 (S103). Accordingly, when the value of the variable n has reached 5 (S17: YES), the control part 21 determines an average value $\Delta I$ of differences $\Delta In-4$ to $\Delta In$ and stores the determined average value $\Delta I$ in the storage part 22 (S104).

Referring to FIG. 8B, when the time of the average value $\Delta T$ has elapsed from the start of the expiratory phase (S23: YES), the control part 21 starts to apply drive voltages to the electrodes 44 and 45 of the electrode unit 4 to facilitate swallowing (S24), and then continues to apply the drive voltages to the electrodes 44 and 45 of the electrode unit 4 until a time obtained by multiplying the average value ΔI by a predetermined ratio R has elapsed from the start of the expiratory phase (S111). In this case, the ratio R is set as 0<R<1, and more desirably is set in such a manner that the application of an electric stimulus is terminated prior to about ⅔ of the expiratory phase. By setting the period of application of an electric stimulus in such a manner, it is possible to prevent an electric stimulus from being applied by mistake in the inspiratory phase.

In the foregoing case, the time obtained by multiplying the average value ΔI by the predetermined ratio R is set as time for terminating the application of an electric stimulus. Alternatively, a time obtained by subtracting a predetermined period of time Δt from the average value ΔI may be set as the time for terminating the application of an electric stimulus. This also makes it possible to prevent the period of application of an electric stimulus from overlapping the inspiratory phase. Also in this case, the period of time Δt is desirably set in such a manner that the application of an electric stimulus is terminated prior to about ⅔ of the expiratory phase.

In the foregoing embodiment, the average value of the differences ΔTn determined with respect to the five expiratory phases preceding the current expiratory phase is set as period of time ΔT with respect to the current expiratory phase. However, the range of the expiratory phases to be averaged is not limited to the five expiratory phases preceding the current expiratory phase, but may be set in another range such as ten expiratory phases preceding the current expiratory phase. In addition, the method for determining the period of time ΔT is not limited to averaging but may be any other method.

Figure 9A:
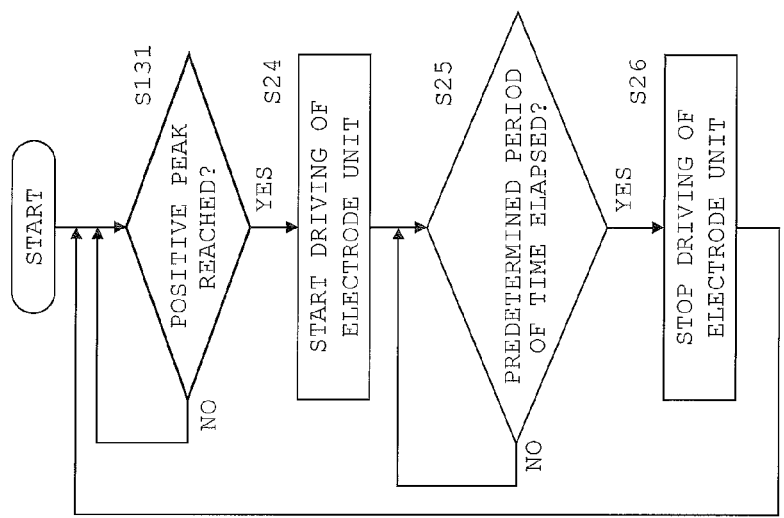
FIGS. 9A to 9C are flowcharts showing processes for controlling the electrode unit according to the modification example.

In addition, in the foregoing embodiment, the average value ΔT is determined according to the differences ΔTn in the five preceding expiratory phases, and the driving of the electrode unit 4 is started at the timing at which the time of the average value ΔT has elapsed from the start of the current expiratory phase. However, the embodiment of the present invention is not limited to this but the driving of the electrode unit 4 may be started at the timing at which a fixed period of time ΔTf has elapsed from the start of the current expiratory phase as illustrated in FIG. 9A. The period of time ΔTf in this case is generally set in advance according to the timing at which the expiration has reached the peak, for example.

FIG. 9A is a flowchart of a process for controlling the electrode unit 4 in the foregoing case. In this case, the process of FIG. 5A in the foregoing embodiment is omitted, and the process of FIG. 9A is performed instead of the process of FIG. 5B in the foregoing embodiment. Referring to FIG. 9A, the step S21 is omitted from the process of FIG. 5B, and step S121 is added in place of the step S23. In this case, when the expiratory phase is started (S22: YES), the control part 21 determines whether the fixed period of time ΔTf stored in the storage part 22 has elapsed (S121). When the period of time ΔTf has elapsed from the start of the expiratory phase (S121: YES), the electrode unit 4 is driven in the same manner as in the foregoing embodiment (S24 to S26). The period of time required at S25 is set at least in such a manner that the application of an electric stimulus is terminated prior to the end of the expiratory phase, more desirably in such a manner that the application of an electric stimulus is terminated prior to about ⅔ of the expiratory phase, as in the foregoing embodiment. Also in this modification example, the time for terminating the application of an electric stimulus may be set according to the timing for starting the inspiratory phase as in the cases of FIGS. 8A and 8B.

Alternatively, immediately after the start of the expiratory phase, the electrode unit 4 may be driven to start the application of an electric stimulus to the patient.

Figure 9B:
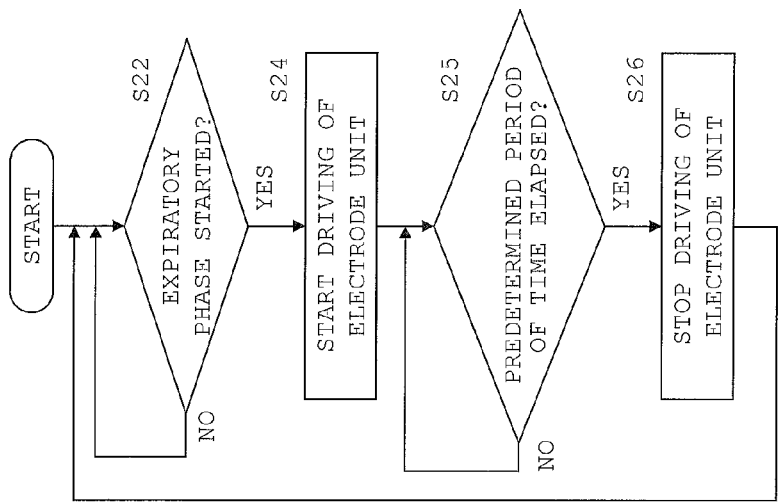

FIG. 9B is a flowchart of a process for controlling the electrode unit 4 in the foregoing case. In this case, the process of FIG. 5A in the foregoing embodiment is omitted, and the process of FIG. 9B is performed instead of the process of FIG. 5B in the foregoing embodiment. Referring to FIG. 9B, the steps S21 and S23 are omitted from the process of FIG. 5B. In this case, when the expiratory phase is started (S22: YES), the control part 21 immediately starts to drive the electrode unit 4 (S24). Then, the electrode unit 4 is driven in the same manner as in the foregoing embodiment (S25 and S26).

According to this modification example, since an electric stimulus is applied immediately after the start of the expiratory phase, it is possible in particular to make longer the period of time until occurrence of the inspiration after the application of an electric stimulus. In addition, since the period of time until the start of the next inspiration is longer, it is possible to provide the sufficient period of time of stimulation, while preventing the period of stimulation from overlapping the inspiratory phase. Accordingly, by facilitation of swallowing immediately after the start of the expiration, it is possible to effectively suppress the possibility that aspiration is caused by the facilitated swallowing.

Also in the modification example, the predetermined period of time at S25 is set at least in such a manner that the application of an electric stimulus is terminated prior to the end of the expiratory phase, more desirably in such a manner that the application of an electric stimulus is terminated prior to about ⅔ of the expiratory phase, as in the foregoing embodiment. Since the expiratory phase is generally about 2000 ms as described above, the predetermined period of time at the step S25 in this case is set at least to 2000 ms or less to prevent the electrode unit 4 from being driven in the inspiratory phase. Further, the predetermined period of time at S25 in this case is desirably set between 100 ms and 1000 ms as described above. When the predetermined period of time is set to 1000 ms or less, the driving of the electrode unit 4 is stopped prior to about ½ of the expiratory phase. Accordingly, it is possible to securely avoid the timing at about ⅔ of the expiratory phase in which the latency time until the next inspiration is shortest. In addition, by setting the predetermined period of time to 100 ms or more, it is possible to securely apply a stimulus to the superior laryngeal nerve. Also in the modification example, the time for terminating the application of an electric stimulus may be set according to the timing for starting the inspiratory phase as in the cases of FIGS. 8A and 8B.

In the foregoing embodiment, the timing at which the expiration reaches the peak is predicted according to the past difference ΔT. Alternatively, the application of an electric stimulus may be started at the timing at which the peak of the expiration is detected.

Figure 9C:
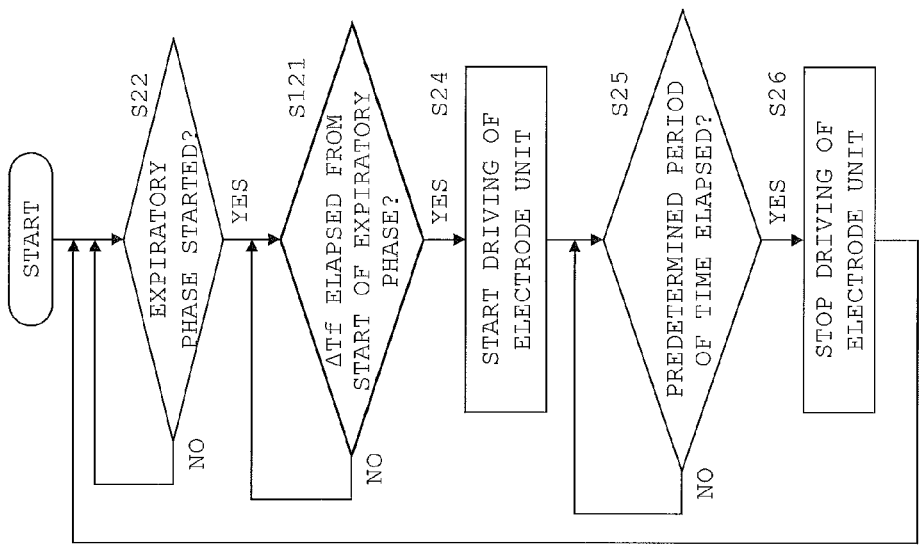

FIG. 9C is a flowchart of a process for controlling the electrode unit 4 in the foregoing case. In this case, the process of FIG. 5A in the foregoing embodiment is omitted, and the process of FIG. 9C is performed instead of the process of FIG. 5B in the foregoing embodiment. Referring to FIG. 9C, the step S21 is omitted from the process of FIG. 5B and the step S131 is added instead of the steps S22 and S23. In this case, the control part 21 determines whether the detection signal has reached the positive peak (S131). When the detection signal has reached the positive peak (S131: YES), the control part 21 immediately starts to drive the electrode unit 4 (S24). Then, the electrode unit 4 is driven in the same manner as in the foregoing embodiment (S25 and S26). Also in the modification example, the predetermined period of time at the step S25 is set at least in such a manner that the application of an electric stimulus is terminated prior to the end of the expiratory phase, more desirably in such a manner that the application of an electric stimulus is terminated prior to about ⅔ of the expiratory phase, as in the foregoing embodiment. Also in the modification example, the time for ending the application of an electric stimulus may be set according to the timing for starting the inspiratory phase as in the cases of FIGS. 8A and 8B.

In the modification example of FIG. 9C, it is assumed that there may arise a time lag (delay) in the process between the timing at which the expiration has actually reached the peak and the timing at which the peak of the expiration is detected in the course of the process. When the time lag is large, the application of an electric stimulus may be started in the second half of the expiratory phase to induce swallowing, for example. Thus, to avoid such an event, it is desired to predict the timing at which the expiration reaches the peak according to the previous differences ΔTn as in the foregoing embodiment. Otherwise, when such a time lag presents no problem, the control process can be simplified by executing the control to the electrode unit 4 as illustrated in FIG. 9C.

In the foregoing embodiment, it is assumed that when the swallowing assist device 1 is attached to the patient and the swallowing assist device 1 is activated, an electric stimulus is constantly applied to the patient over the entire period of time from the activation to the stoppage of the swallowing assist device 1. However, the embodiment of the present invention is not limited to this but the electrode unit 4 may be controlled over the entire period of time from the activation to the stoppage of the swallowing assist device 1 in such a manner as to set alternately the period of time during which an electric stimulus is applied to the patient and the period of time during which an electric stimulus is not applied to the patient.

Figure 10A:
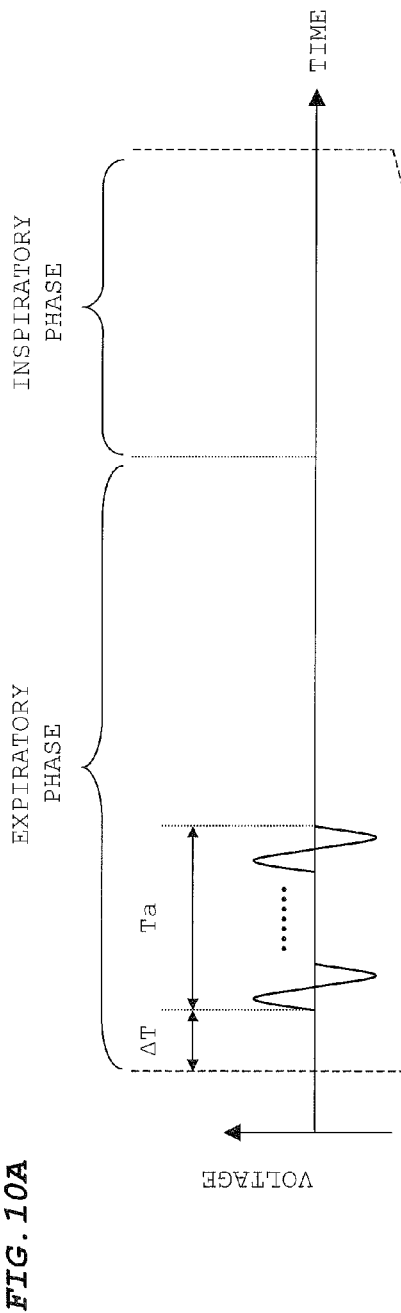
FIGS. 10A and 10B are schematic diagrams illustrating the timings for driving the electrode unit according to the modification example.
Figure 10B:
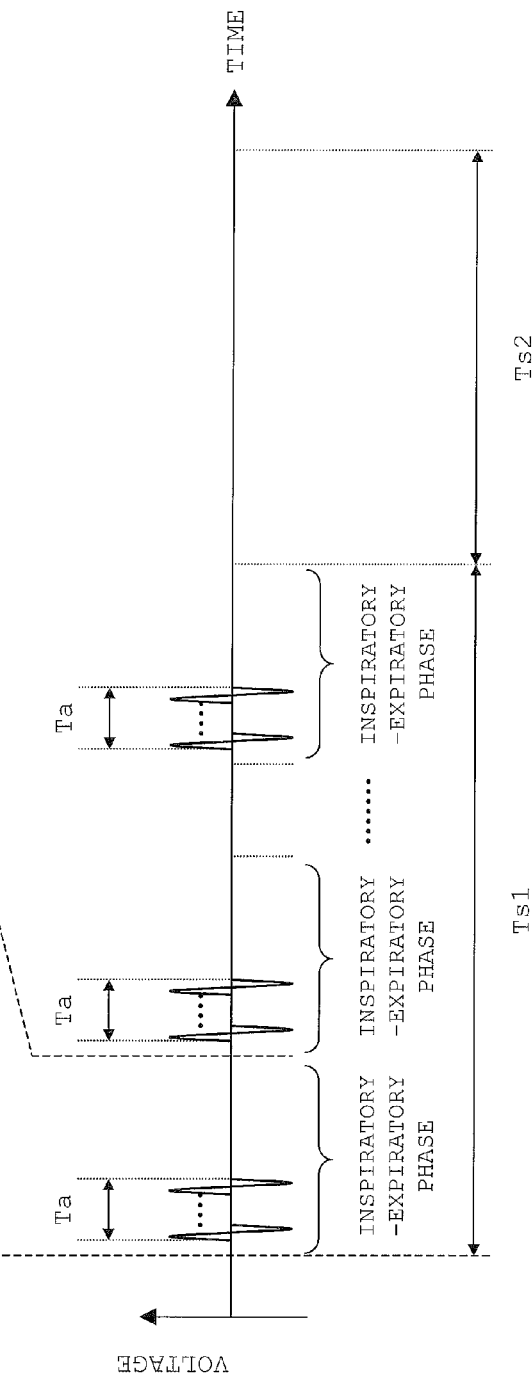

FIGS. 10A and 10B are schematic diagrams illustrating timings for driving the electrode unit 4 in this case. In the foregoing embodiment, as illustrated in FIG. 10A, when the time of the average value ΔT has elapsed from the start of the expiratory phase, a voltage is applied to the electrode unit 4 for a predetermined period of time (Ta in the example of FIG. 10A). During the period of time corresponding to the time Ta, the sinusoidal signals are applied to the electrodes 44 and 45 as described above with reference to FIGS. 3B and 3C. Then, in the modification example, an electric stimulus illustrated in FIG. 10A is applied for a period of time Ts1 as illustrated in FIG. 10B. After lapse of the period of time Ts1, the application of an electric stimulus is stopped during a period of time Ts2. The period of times Ts1 and Ts2 are set to 60 minutes and 30 minutes, respectively, for example.

Figure 11B:
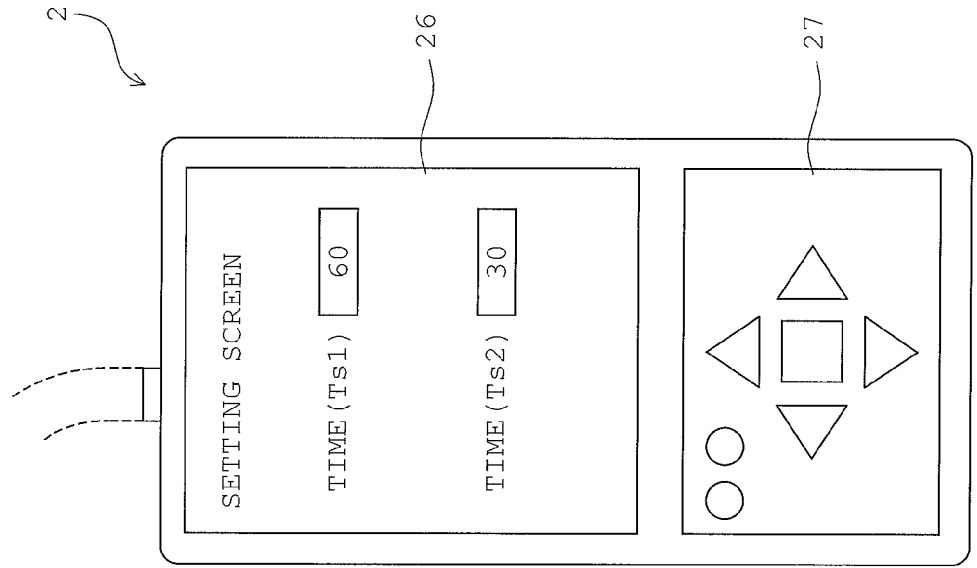
FIGS. 11A and 11B are respectively a flowchart of a process for controlling the electrode unit and a diagram illustrating a display part and an input part of a control unit according to the modification example.
Figure 11A:
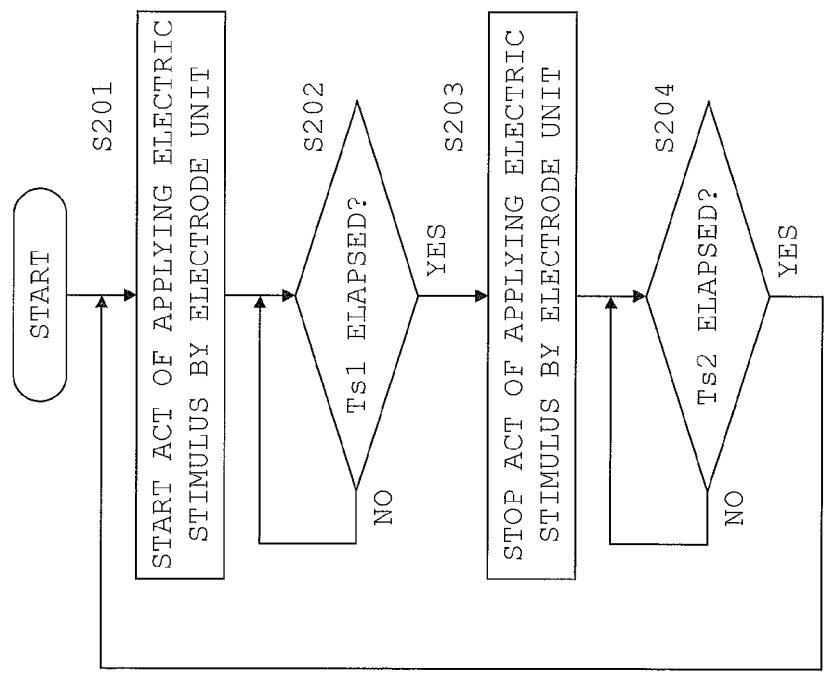

FIG. 11A is a flowchart of a process for controlling the electrode unit 4 in this case. When the swallowing assist device 1 is activated, the control part 21 causes the electrode unit 4 to start the act of applying an electric stimulus (S201). Accordingly, the electrode unit 4 is controlled as described in FIGS. 5A and 5B. Then, when the time Ts1 has elapsed from the start of the act of applying an electric stimulus by the electrode unit 4 (S202: YES), the control part 21 causes the electrode unit 4 to stop the act of applying an electric stimulus (S203). Accordingly, the controls of the electrode unit 4 described in FIGS. 5A and 5B are stopped. Then, when the time Ts2 has elapsed from the stoppage of the act of applying an electric stimulus by the electrode unit 4 (S204: YES), the control part 21 returns the process to S201. Accordingly, the driving of the electrode unit 4 as described in FIGS. 5A and 5B is performed on a cyclical basis.

The times Ts1 and Ts2 may be set by the user as appropriate. In this case, as illustrated in FIG. 11B, for example, input boxes for setting the times Ts1 and Ts2 are included in a setting screen on the display part 26 of the control unit 2. When the buttons on the input part 27 are operated, the times Ts1 and Ts2 in the input boxes are changed. Accordingly, it is possible to set arbitrarily the times Ts1 and Ts2 according to the patient's swallowing function.

In the modification example, the times Ts1 and Ts2 are kept constant over the entire operating time of the swallowing assist device 1. Alternatively, the control in which the times Ts1 and Ts2 are changed after the activation of the swallowing assist device 1 may be executed. For example, the control in which the time Ts1 for applying an electric stimulus is decreased over time after the activation of the swallowing assist device 1 may be executed. More specifically, when the time Ts1 immediately after the activation of the swallowing assist device 1 is set to 60 minutes, the control part 21 then drives the electrode unit 4 with the time Ts1 of 60 minutes until the number of the period of application of an electric stimulus has reached to a predetermined number of times (for example, three times), and after that, the control part 21 drives the electrode unit 4 with the time Ts1 decreased by a predetermined period of time (for example, ten minutes) each time the period of application of an electric stimulus comes. Accordingly, it is possible to decrease the degree of an electric stimulus according to the recovery of the patient's swallowing function by the action of medical treatment.

When the electrode unit 4 is controlled in such a manner as to be in the operating state and the non-operating state alternately as described above, it is possible to reduce the burden on the patient resulting from an electric stimulus. In addition, it is possible to suppress the accommodation of the superior laryngeal nerve to the electric stimulus and enhance the effect of facilitating swallowing by the electric stimulus.

In the foregoing embodiment, the swallowing assist device 1 is used for the human patient. Alternatively, the swallowing assist device 1 may be used for animals.

In the foregoing embodiment, the nasal cannula 3 is used to detect the patient's respiration. However, the embodiment of the present invention is not limited to this but, instead of the nasal cannula 3, a mask with a tube, a catheter to be inserted into the mouth cavity or trachea, or any other device for transferring the flow of air by respiration. In addition, the respiration of the patient may be detected not from the flow of air caused by respiration but from a change in the patient's chest volume or from the patient's breathing sounds.

In the foregoing embodiment, the nasal cannula 3 is included as a component of the swallowing assist device 1. However, for the swallowing assist device described in the claims, such tools to be directly attached to the patient as a nasal cannula are not necessarily essential components. That is, the swallowing assist device described in the claims can be applied to not only transaction modes including tools such as a nasal cannula but also transaction modes not including tools such as a nasal cannula.

In the foregoing embodiment, the pad 41 with the electrodes 43 is attached to the surface of the patient's neck skin. However, the embodiment of the present invention is not limited to this but the electrodes 43 may be arranged subcutaneously at the patient's neck.

Besides, the embodiment of the present invention can be modified in various manners within the scope of the technical ideas described in the claims.

A principal aspect of the embodiment of the present invention relates to a swallowing assist device for assisting swallowing. The swallowing assist device according to the aspect includes: a respiration detection part that detects respiration; an application unit that is attached to a target section to apply a stimulus for facilitation of swallowing; and a control part that controls the application unit. The control part controls the application unit to start application of the stimulus to the target section during an expiration period detected according to a detection signal from the respiration detection part, and terminates the application of the stimulus to the target section during the expiration period.

Obviously, numerous modifications and variations of the present invention are possible in light of the above teachings. It is therefore to be understood that within the scope of the appended claims, the invention may be practiced otherwise than as specifically described herein.

What is claimed is:

1. A swallowing assist device for assisting swallowing, comprising:
   a respiration detection part that detects respiration;
   an application unit that includes an electrode with a positive pole and an electrode with a negative pole, the application unit being configured to be attached to a target section to apply an electric stimulus for facilitation of swallowing; and
   a control part that controls the application unit, wherein the control part is programmed to control the application unit to start application of the electric stimulus to the target section based on the detection of an expiration period according to a detection signal from the respiration detection part, to terminate the application of the electric stimulus to the target section during the expiration period, and to modify the start of the application of the electric stimulus in response to the detection signal from the respiration detection part.

2. The swallowing assist device according to claim 1, wherein the control part controls the application unit such that a timing for starting the application of the electric stimulus to the target section falls within a first half of an expiratory phase.

3. The swallowing assist device according to claim 2, wherein the control part detects a start of the expiratory phase according to the detection signal from the respiration detection part, and controls the application unit to start the application of the electric stimulus to the target section immediately after the start of the expiratory phase.

4. The swallowing assist device according to claim 2, wherein the control part detects a timing at which an expiration has reached a peak according to the detection signal from the respiration detection part, and controls the application unit to start the application of the electric stimulus to the target section at the timing at which the expiration has reached the peak.

5. The swallowing assist device according to claim 1, wherein the control part controls the application unit such that a timing for terminating the application of the electric stimulus to the target section is earlier than a timing at ⅔ of an expiratory phase.

6. The swallowing assist device according to claim 1, wherein a period of time from a timing for starting the application of the electric stimulus to a timing for terminating the application of the electric stimulus is set between 100 ms and 1000 ms.

7. The swallowing assist device according to claim 1, wherein, on activation of the swallowing assist device, the control part alternately sets an operating time during which an operation to apply the electric stimulus to the target section in the expiration period is executed and a non-operating time during which the operation to apply the electric stimulus to the target section in the expiration period is not executed.

8. The swallowing assist device according to claim 7, further comprising an acceptance part that accepts settings of the operating time and the non-operating time.

9. The swallowing assist device according to claim 1, wherein the application unit is configured to be attached to a skin to apply the electric stimulus to a superior laryngeal nerve.

10. The swallowing assist device according to claim 9, wherein
   the application unit is provided with two pairs of the electrodes, and
   the control part applies electric signals at different frequencies to the two pairs of the electrodes.

11. The swallowing assist device according to claim 10, wherein the two pairs of electrodes are disposed in an X-formation.

12. The swallowing assist device according to claim 1, wherein the respiration detection part comprises a sensor, and the control part is configured to control the application unit to start application of the electric stimulus in response to the detection signal transmitted from the sensor.

13. A swallowing assist device comprising:
   a respiration detection part that detects respiration;
   an application unit that includes an electrode with a positive pole and an electrode with a negative pole, the application unit being configured to be attached to a target section to apply an electric stimulus for facilitation of swallowing; and
   a control part that controls the application unit, wherein the control part controls the application unit to start application of the electric stimulus to the target section based on the detection of an expiration period according to a detection signal from the respiration detection part, and terminate the application of the electric stimulus to the target section during the expiration period, and
   wherein the application unit further comprises a pad in which the electrode with the positive pole and the electrode with the negative pole are disposed, the pad being configured to be attached to a skin to apply the electric stimulus.

14. The swallowing assist device according to claim 13, wherein the application unit is provided with two pairs of electrodes disposed in an X-formation, and
   wherein the control part simultaneous applies electric signals at different frequencies to the two pairs of the electrodes.

* * * * *